United States Patent
Arbona Celaya et al.

(10) Patent No.: US 10,072,238 B2
(45) Date of Patent: Sep. 11, 2018

(54) MICROALGAE CULTURE SYSTEM UNDER EXTERNAL CONDITIONS

(75) Inventors: Andres Arbona Celaya, Sarriguren (ES); Miguel De La Parra Abad, Sarriguren (ES); Ivan Ripa Ngkaion, Sarriguren (ES); Mikel Sojo Armentia, Sarriguren (ES)

(73) Assignee: Acciona Energia, S.A., Sarriguren (Navarra) (ES)

( * ) Notice: Subject to any disclaimer, the term of this patent is extended or adjusted under 35 U.S.C. 154(b) by 19 days.

(21) Appl. No.: 14/411,903

(22) PCT Filed: Jul. 3, 2012

(86) PCT No.: PCT/ES2012/070489
§ 371 (c)(1),
(2), (4) Date: Dec. 29, 2014

(87) PCT Pub. No.: WO2014/006233
PCT Pub. Date: Jan. 9, 2014

(65) Prior Publication Data
US 2015/0184118 A1    Jul. 2, 2015

(51) Int. Cl.
*C12M 1/00* (2006.01)
*C12M 3/00* (2006.01)
(Continued)

(52) U.S. Cl.
CPC ............ *C12M 21/02* (2013.01); *C12M 23/04* (2013.01); *C12M 23/18* (2013.01); *C12M 27/02* (2013.01);
(Continued)

(58) Field of Classification Search
CPC ...... C12M 21/02; C12M 23/04; C12M 23/18; C12M 27/02; C12M 27/06; C12M 29/06; C12M 39/00
(Continued)

(56) References Cited

U.S. PATENT DOCUMENTS

| 4,320,594 A | 3/1982 | Raymond |
| 8,806,697 B1 * | 8/2014 | Davila, Jr. ............ B08B 9/0808 15/246.5 |

(Continued)

FOREIGN PATENT DOCUMENTS

WO    WO 2011/029178 A1    3/2011

OTHER PUBLICATIONS

PCT International Search Report for PCT Counterpart Application No. PCT/ES2012/070489, 5 pages (including English translation), (dated Apr. 2, 2013).

*Primary Examiner* — Michael L Hobbs
(74) *Attorney, Agent, or Firm* — Womble Bond Dickinson (US) LLP

(57) ABSTRACT

The present invention relates to a microalgae culture system under external conditions that comprises a shallow-depth culture container, a rotation system for the generation of light-darkness cycles and re-suspension, which maximises the photosynthetic efficiency of the microalgae and homogenises the nutrients supplied such that the microalgae may adequately grow in all the areas of the photobioreactor, a gas exchange and temperature control system, which makes it possible to control and maintain the culture parameters under the optimal microalgae growth conditions, a filtration and self-cleaning system, an energy control and saving system, which makes it possible to maintain the desired conditions with the lowest energy expenditure, and a cover system, which filters ultraviolet and/or infrared radiation and makes it possible to control contaminations, the temperature and the evaporation.

15 Claims, 3 Drawing Sheets

(51) Int. Cl.
*C12M 1/06* (2006.01)
*C12M 1/12* (2006.01)

(52) U.S. Cl.
CPC ............ *C12M 27/06* (2013.01); *C12M 29/06* (2013.01); *C12M 39/00* (2013.01)

(58) Field of Classification Search
USPC .......................................... 435/292.1; 47/1.4
See application file for complete search history.

(56) References Cited

U.S. PATENT DOCUMENTS

2003/0073231 A1\* 4/2003 Dutil ..................... C12M 21/02
435/292.1
2010/0190236 A1 7/2010 Delobel
2010/0297705 A1\* 11/2010 Medoff .................. C12M 45/02
435/72

\* cited by examiner

MICROALGAE CULTURE SYSTEM UNDER EXTERNAL CONDITIONS

CROSS-REFERENCE TO RELATED APPLICATION

This patent application is a U.S. National Phase Application under 35 U.S.C. § 371 of International Application No. PCT/ES2012/070489, filed Jul. 3, 2012, entitled MICROALGAE CULTURE SYSTEM UNDER EXTERNAL CONDITIONS.

FIELD OF THE INVENTION

The present invention belongs to the technical field of microalgae production. Specifically, it falls within the area of culture systems designed for the mass production of microalgae under external conditions.

OBJECT OF THE INVENTION

The object of the patent is an optimised microalgae culture system that comprises a shallow-depth culture container, a rotation system designed for the generation of light-darkness cycles and re-suspension, which maximises the photosynthetic efficiency of the microalgae and homogenises the nutrients supplied, such that the microalgae may adequately grow in all the areas of the photobioreactor, a gas exchange and temperature control system, which makes it possible to control and maintain the culture parameters under the optimal microalgae growth conditions, a filtration and self-cleaning system, an energy control and saving system, which makes it possible to maintain the desired conditions with the lowest energy expenditure, and a cover system, which filters ultraviolet radiation and makes it possible to control contaminations, the temperature and the evaporation. All this with low investment, minimum energy consumption and high culture efficiency.

BACKGROUND OF THE INVENTION

Microalgae are proving to be of great utility because they present a large number of beneficial applications in various different areas, such as wastewater treatment, production of biofuels, food for humans and animals, and the obtainment of high-value chemical products. Microalgae cultures may reach productivities that are much higher than those of traditional cultures, leading to a greater $CO_2$ fixation and a larger quantity of biomass produced. Moreover, microalgae cultures have lower water requirements and do not compete with traditional cultures, since they do not need fertile soil or potable water.

In order to obtain an optimal profitability in large-scale microalgae production projects, large areas, in addition to sufficiently large industrial facilities, are needed in order to justify the necessary investments. Microalgae production systems primarily include two differentiated classes: closed systems and open systems. Closed systems are characterised in that they insulate the fluid from the external environment and are less exposed to disturbances, whereas open systems are characterised in that they have a greater interaction with or exposure to the environment and are more dependent on the conditions thereof.

Microalgae production systems are equipped with devices designed to extract the microalgae once they are generated; this is what is called "harvesting". They are also equipped with devices designed for the inclusion of new culture media, where culture medium is understood to mean the set of nutrients dissolved in water which the microalgae need, as well as for the stirring and reduction of concentration gradients, the elimination of oxygen and the absorption of carbon dioxide in the culture medium.

In microalgae production systems, the following factors must be taken into consideration in order to achieve the maximum yield:

Oxygen at high concentrations may be toxic for the microalgae, especially when there is a high solar radiation, Microalgae perform photosynthesis and, therefore, should have sufficient light available, although an excess of light may be harmful. Microalgae should not remain in permanent darkness, and an optimal light exposure frequency makes it possible to optimise the productivity, The nutrients supplied should be homogenised, such that the microalgae may grow in all the areas of the system, The $CO_2$ should be distributed throughout the entire culture system, such that the microalgae may fixate this $CO_2$, The decanting of microalgae in dead zones of the culture systems should be avoided, since, in addition to entailing a loss of productivity, because these cells do not have access to light, the decanted cells may be a contamination focus, The culture systems should be kept clean, in order to prevent contaminations that may affect the growth of the microalgae, The microalgae cultures should be kept within an appropriate temperature range, in order to optimise the productivity and prevent cell death caused by cold or excessive heat.

The microalgae culture systems known by the applicant are either tubular systems that may be closed or large bags, preferably made of a plastic material, which present a high energy consumption to obtain an acceptable yield in microalgae production.

SUMMARY OF THE INVENTION

The present invention relates to a high-productivity, low-investment microalgae culture system under external conditions optimised for microalgae production, which makes it possible to generate light-darkness cycles in the system, the cleaning and maintenance thereof under optimal production conditions, with minimum energy consumption, i.e. with a high efficiency.

The culture system comprises:

a shallow-depth culture medium container, where shallow depth is understood to mean a tank wherein the ratio between the height "h" of the culture medium, in m, and the surface area "A" of the base of the container, in $m^2$, meets the condition that $$\frac{h}{\sqrt[4]{A}} < 0.12.$$

This characteristic makes it possible to work with high cellular concentrations, since there is less contamination and the "downstream" cost is reduced; moreover, there is a low investment cost, since no support structures are required, and there is also easy climbing.

a rotation system equipped with at least some rotating means.

a culture medium that may be vertically displaced by the rotating means, to generate a turbulent regime in the culture medium, where the rotating means are preferably composed of a set of rotating blades. These blades may have the following functions:

They may be blades that generate light-darkness cycles in the culture medium. They produce movement in the culture, thereby preventing the stratification thereof, increasing its homogeneity and, consequently, considerably increasing the productivity. This system gives priority to the vertical movement, thereby minimising the energy consumption, in addition to being easily climbable by increasing the number and length of the blades, and/or sweep blades, the mission whereof is to re-suspend the algae deposited and clean potential contaminations at the bottom of the container. This re-suspension makes it possible to keep the entire cell population under continuous growth, generating a greater quantity of biomass and, consequently, increasing the productivity. The self-cleaning system makes it possible to increase the number of working days and simultaneously reduce the labour costs necessary for the operation thereof, and/or blades equipped with deflection means the mission whereof is to adapt the movement of the fluid, decreasing the mixing times, favouring the homogeneity of the system and, consequently, increasing the efficiency and productivity thereof.

The culture system further comprises a $CO_2$ fixation and $O_2$ desorption system for the simultaneous transfer of both matter and heat. The $CO_2$ fixation and $O_2$ desorption system preferably has the shape of a pit the bottom whereof contains diffusers that supply $CO_2$ or mixtures of $CO_2$ with other combustion gases in order to carry inorganic carbon, and/or air in order to desorb the excess $O_2$ that may accumulate. These diffusers are high-efficiency diffusers, in order to achieve a high matter transfer coefficient whilst minimising the energy consumption. This same pit contains a heat exchanger that makes it possible to control the temperature of the culture medium or the thermostatting thereof. This pit may be integrated in the interior of the culture medium container (1) or in the exterior thereof, preferably buried. In the latter case, a pump is used to force passage of the entire culture medium through the $CO_2$ fixation, $O_2$ desorption and thermostatting system.

The culture system further comprises a surface filtration system that makes it possible to remove potential contaminations and foreign elements with a lower density than the culture medium and a larger size than the microalgae. No additional labour or maintenance is required, which increases the cleanliness and productivity, since shadows, i.e. lack of irradiance, are avoided and the hygiene of the culture is improved.

The culture system further comprises an energy control and saving system that records pluviometric, radiation, pH, temperature and dissolved oxygen data and acts on the injection of $CO_2$, the air supply, the rotation system and the system cover. This energy control and saving system makes it possible to maintain the optimal working conditions with the lowest energy consumption and hardly any labour or supervision.

The culture system further comprises a transparent cover system. The purpose of the cover is to better control the temperature, prevent contaminations, filter ultraviolet and infrared radiation, and reduce the water consumption by controlling the evaporation thereof. It is possible to place a central axis perpendicular to the flat culture medium container, whereon the cover is supported, descending down to the perimeter thereof. This system is very economical due to the absence of complicated structures.

The culture system further comprises a water replacement device that may operate alternatively or jointly with the cover system to introduce water into the culture medium container and thus keep the volume of water at the required levels. The culture system further comprises a harvesting system designed for the extraction of the microalgae once the growth process thereof is completed, and a culture medium supply system.

BRIEF DESCRIPTION OF THE DRAWINGS

In order to supplement the description, and contribute to a better understanding of the characteristics of the invention, a set of drawings is attached as an integral part of said description, for illustrative, non-limiting purposes. The following has been represented.

Figure 1:
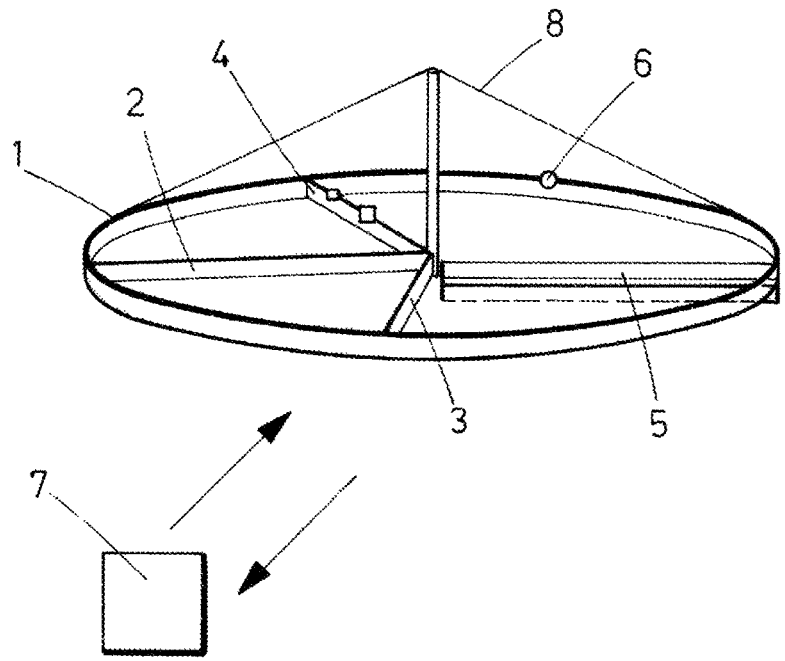
FIG. 1.—Shows the microalgae culture system under external conditions of the present invention with a first embodiment of the $CO_2$ fixation and $O_2$ desorption system.

Description of the Elements that Make Up the System:

Element 1 represents the culture medium container.

Element 2 represents the rotating blades that allow for the generation of light-darkness cycles.

Element 3 represents the rotating blades that sweep and re-suspend the culture.

Element 4 represents the rotating blades, equipped with deflectors capable of modifying the flow of the fluid inside the culture medium container.

Element 5 represents a schematic view of the carbon dioxide fixation and oxygen desorption system placed inside the area delimited by the culture medium container (1).

Element 6 represents a schematic view of the surface filtration system.

Element 7 represents a schematic view of the energy control and saving system that makes it possible to optimise the energy consumption.

Element 8 represents a schematic view of the cover system.

DETAILED DESCRIPTION OF THE INVENTION

In light of the figures, we describe several preferred embodiments of the culture system that comprises a shallow-depth, flat culture medium container with a circular base (1), where shallow depth is understood to mean a container wherein the ratio between the height "h" of the culture medium and the surface area "A" of the base of the container meets the condition that $$\frac{h}{\sqrt[4]{A}} < 0.12,$$

a rotation system that comprises at least rotating means designed to vertically displace the culture medium, thereby generating a turbulent regime, where these rotating means are preferably composed of a set of rotating blades (2) around a vertical central axis of the container for the generation of light-darkness cycles.

The rotation system further comprises a set of sweep blades (3) that clean the container surfaces and a set of deflector blades (4), or blades equipped with deflection means, the mission whereof is to adapt the movement of the fluid, thereby decreasing the mixing times.

The culture system further comprises one or several carbon dioxide fixation and oxygen desorption systems (5), which further comprise thermostatting means, as well as a surface filtration system (6), an energy control and saving system, which makes it possible to optimise the energy consumption (7), and a cover system (8).

First Preferred Embodiment

In a first preferred embodiment, shown in FIG. 1, the carbon dioxide fixation and oxygen desorption system (5), which further comprises thermostatting means, is located inside the area delimited by the culture medium container (1), extends from the centre to the periphery thereof along the entire radius and has the shape of a pit. The carbon dioxide fixation and oxygen desorption system (5) comprises a gas injection system placed on the lower part of the pit, which comprises diffusers that inject air, $CO_2$ or mixtures of $CO_2$ with other combustion gases in order to supply inorganic carbon and/or air to desorb the excess $O_2$ that may accumulate.

The gas injection system further comprises a gas flow rate regulator valve that makes it possible to regulate the desorption of oxygen from the culture medium, since oxygen at high concentrations is toxic for the microalgae. This same pit houses an exchanger that makes it possible to control the temperature of the culture medium.

The profile of the rotating blades (2) designed for the generation of light-darkness cycles has the shape of a fin, and the attack edge of the profile of the rotating blades (2) is closer to the bottom of the circular-base container (1) than the outlet edge of said rotating blades (2) designed for the generation of light-darkness cycles, where the attack edge is not on the same vertical line as the outlet edge. This configuration makes it possible to increase the turbulence in the culture medium downstream from the blades, thereby favouring the displacement of the culture medium in the vertical direction.

Therefore, the culture system performs several functions simultaneously:
   to efficiently desorb the $O_2$,
   to efficiently fixate the $CO_2$,
   to generate light-darkness cycles with a low energy cost,
   to thermostat the culture medium,
   to prevent the microalgae from depositing,
   to homogenise the nutrients,
   to homogenise the available $CO_2$.

Second Preferred Embodiment

Figure 2:
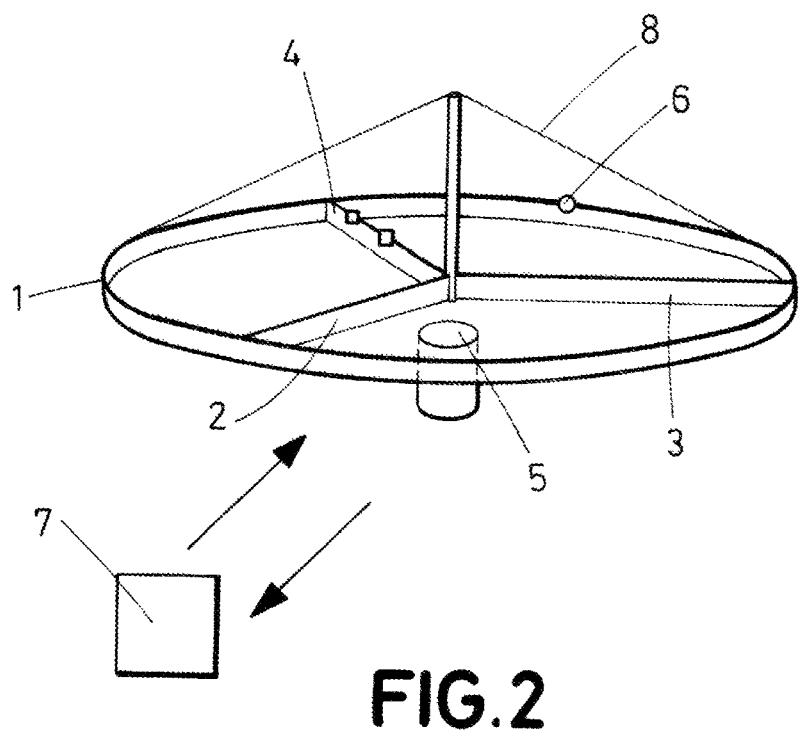
FIG. 2.—Shows the microalgae culture system under external conditions of the present invention with a second embodiment of the $CO_2$ fixation and $O_2$ desorption system.

In a second preferred embodiment, shown in FIG. 2, the carbon dioxide fixation and oxygen desorption system (5), which further comprises thermostatting means, is located inside the area delimited by the culture medium container (1), at the centre of the tank, and has the shape of a pit. The carbon dioxide fixation and oxygen desorption system (5) comprises a gas injection system located on the lower part of the pit, which comprises diffusers that inject air, $CO_2$ or mixtures of $CO_2$ with other combustion gases in order to supply inorganic carbon and/or air to desorb the excess $O_2$ that may accumulate.

The rest of the elements of the culture system are those described in the first preferred embodiment and perform the same functions simultaneously.

Third Preferred Embodiment

Figure 3:
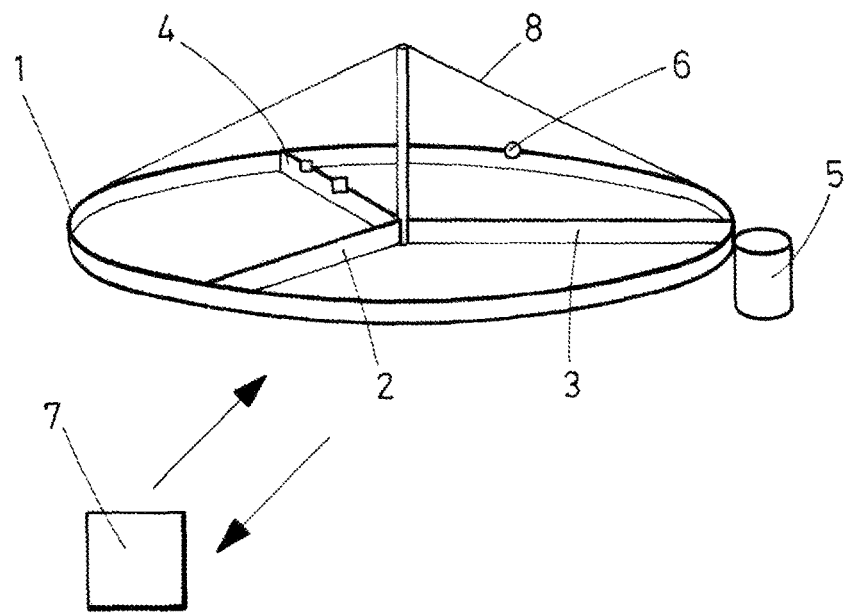
FIG. 3.—Shows the microalgae culture system under external conditions of the present invention with a third embodiment of the $CO_2$ fixation and $O_2$ desorption system.

In a third preferred embodiment, shown in FIG. 3, the carbon dioxide fixation and oxygen desorption system (5), which further comprises thermostatting means, is located outside the area delimited by the culture medium container (1) and is arranged in the shape of a pit below the base of the container (1). The carbon dioxide fixation and oxygen desorption system (5) comprises a gas injection system located on the lower part of the pit which comprises diffusers that inject air, $CO_2$ or mixtures of $CO_2$ with other combustion gases to supply inorganic carbon and/or air to desorb the excess $O_2$ that may accumulate.

The rest of the elements of the culture system are those described in the first preferred embodiment and perform the same functions simultaneously.

Fourth Preferred Embodiment

Figure 4:
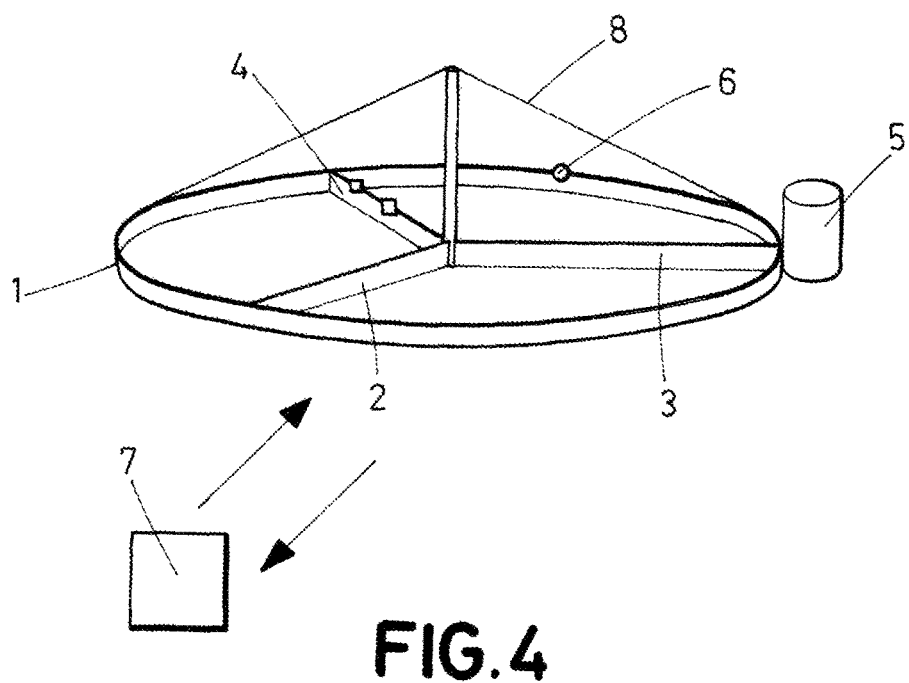
FIG. 4.—Shows the microalgae culture system under external conditions of the present invention with a fourth embodiment of the $CO_2$ fixation and $O_2$ desorption system.
Figure 5:
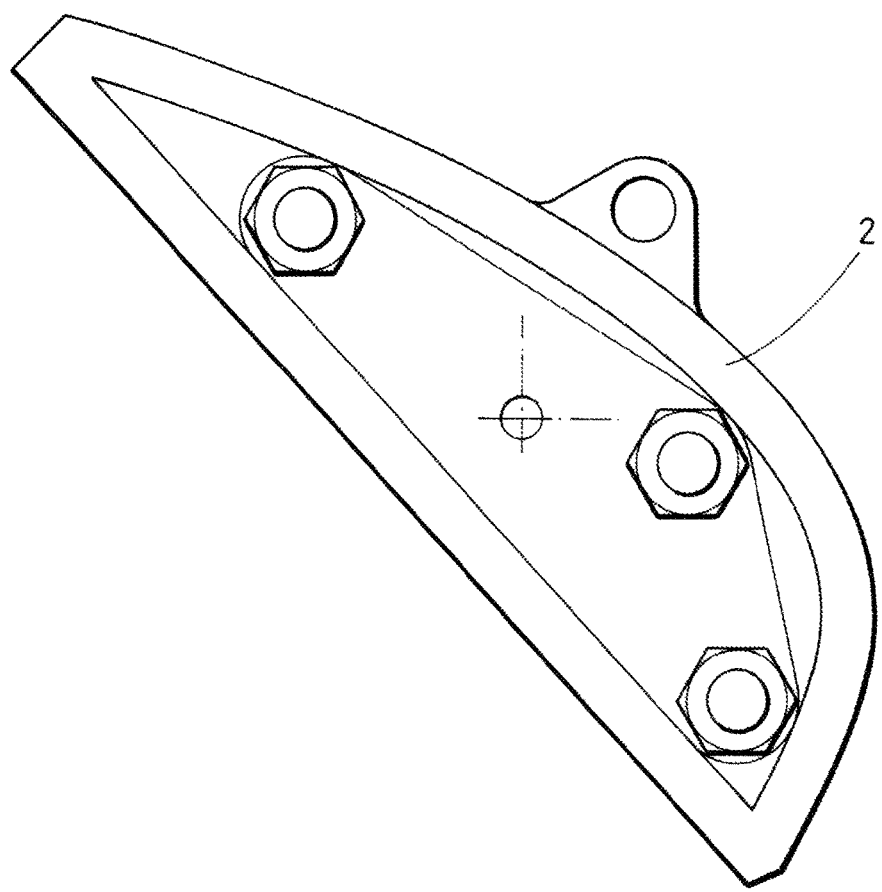
FIG. 5.—Shows a profile view of the blades that generate the light-darkness cycles in the culture medium.

In a fourth preferred embodiment, shown in FIG. 4, the carbon dioxide fixation and oxygen desorption system (5), which further comprises thermostatting means, is located outside the area delimited by the culture medium container (1), at the level of the base of the container (1). The carbon dioxide fixation and oxygen desorption system (5) comprises a gas injection system located on the lower part of the carbon dioxide fixation and oxygen desorption system (5) which comprises diffusers that inject air, $CO_2$ or mixtures of $CO_2$ with other combustion gases to supply inorganic carbon and/or air to desorb the excess $O_2$ that may accumulate.

In this case, the system is equipped with a pump that allows for the exit of the culture from the container (1) towards the $CO_2$ fixation and $O_2$ desorption system (5), and the return hereto.

The rest of the elements of the culture system are those described in the first preferred embodiment and perform the same functions simultaneously.

Below we will describe in detail the auxiliary systems that may be a part of the culture system described in any of the aforementioned embodiments.

1. A cover system that makes it possible to convert the culture system into a closed system, where the height of the rotating vertical axis protrudes from the upper edge of the culture container (1), such that a cover is fixed to a rotating vertical axis and covers the entire upper perimeter of the culture container, transforming it into a greenhouse, the cover being preferably made of plastic. Preferably, it may also be made of a transparent plastic that filters ultraviolet and/or infrared radiation.

Thus, this cover system makes it possible to convert the culture system into a closed system, with the following added advantages:
   External contamination is prevented.
   The culture temperature may be kept more stable against external variations.
   Certain wavelengths may be filtered by installing a cover made of a given material.

It is possible to control the evaporation; therefore, less water is lost and the sustainability of the system increases.

2. An energy control and saving system that optimises the energy consumption as a function of the concentration of $O_2$ and the pH of the culture medium, which comprises one or several of the following elements:

One or more pH meters.
One or more oxygen meters.
A rotational speed variator for the system.

The energy control and saving system comprises a control device that receives a signal of the concentration of oxygen dissolved in the culture. If this value is greater than a pre-determined value, it acts on the desorption system, causing an increase in the transfer of matter and the consequent decrease in the level of dissolved oxygen.

Alternatively, the energy control and saving system may receive two or more signals of the pH of the culture. One of these two measured signals is located far from the point of injection of the carbon dioxide and is used to regulate the dosage of $CO_2$. The other measured signal, located considerably far from the first measured signal, indicates the homogeneity of the system. If the difference between the reading values of the two measurements is greater than a previously set value, the system acts on the rotational speed variator and on the desorption and cleaning system in order to improve the mixing inside the culture system and, consequently, the homogeneity thereof.

A typical situation where there may be substantial differences in the pH of different areas of the container (1) occurs when new culture medium is added to the container (1), since it is added at a specific point. Therefore, in this case, different pHs are detected in different areas and the system acts to reduce the mixing time of the entire culture. When the culture is homogenised, preventing differences in the concentration of $CO_2$, there is an energy saving, because the rotation of the rotating axis is regulated as a function of the needs. In this way, the energy saving system makes it possible to operate the rotation system such that it is efficient as a function of the different variables associated with microalgae production.

3. A water replacement system that may operate alternatively or jointly with the cover system to introduce water into the culture container (1), and thus keeps the volume of water at optimal levels, since in open systems water is continuously evaporated.

This water replacement system comprises the following elements:

Level meter,
Water impeller

When the level meter detects a level of liquid in the culture container (1) that is below a certain value, the water impeller is acted on in order to make water go into the container (1) until the necessary level is completed. Preferably, the level meter comprises a buoy or float which, when the level of liquid in the container (1) decreases, acts as a mechanical switch, and acts on an electrovalve that allows for the passage of water to refill the container (1) with water.

4. A harvesting system designed for the extraction of the microalgae once the growth process is completed, as well as cleaning systems for the bottom and/or walls of the container (1), and culture medium injection systems.

The harvesting system comprises a pump that makes it possible to extract the microalgae, or the harvesting may be performed by gravity extraction, taking advantage of gravity such that the harvested algae fall towards a reservoir; to this end, regardless of the case, it comprises a chute with a sufficient slope, which is integrated at the bottom of the culture container (1).

The chute fulfils a two-fold function: it accumulates dirt and allows for easy harvesting, either by gravity, by placing a tank at a lower height than the chute, or by forced circulation through the pump.

In order to help to carry the dirt to the chute, one or several cleaning brushes are coupled to the elements that generate the light-darkness cycles; these brushes slightly touch the bottom of the container (1) in order to gradually carry what is accumulated in the bottom of the container (1) towards the chute. Thus, the dirt will accumulate in the chute, since, when the brush passes through the chute, it will let the dirt fall, thanks to gravity, to the bottom thereof. In this way, the chute is capable of accumulating the solid sediments and makes it possible to remove a large part of the sediments that are not microalgae.

Preferably, the chute is arranged from the centre of the container (1) to the perimeter of the container (1), where there is an opening that may act as a harvesting point.

Regardless of the presence of the chute, the cleaning brushes coupled to the means that rotate around a plane parallel to the base of the container (1) touch the base of the container (1), the wall of the container (1), or both. Moreover, the shape of the part of these brushes that touches the wall makes it possible for them to displace the dirt towards the upper part of the perimeter of the container (1), and is even able to expel the dirt outside the container (1). Alternatively, thanks to the shape thereof, the part of the brushes that touches the wall directs the dirt towards the lower part of the perimeter of the container (1), thereby bringing together the dirt from the wall and the dirt from the base, for the subsequent cleaning thereof, either through the dirt falling into the chute or by means of periodic maintenance. The brushes are placed on the sweep blades described above.

In both cases, the continuous cleaning, i.e. the fact that the brushes always rotate with the rotation of the vertical rotating support, allows for exhaustive cleaning of the container (1). However, the friction generated by the brushes when they move through the bottom or the walls may increase the energy consumption in the rotation; for this reason, the cleaning brushes may be associated with a brush engagement system that allows for the brushes to operate only during certain given time intervals.

5. A culture medium injection device, which feeds the culture system container (1).

All the systems comprised in the culture system are controlled by a central control system that evaluates all the system variables and sends the appropriate instructions to each of the actuators.

What is claimed is:

1. A microalgae culture system under external conditions comprising:
a shallow-depth culture medium container comprising a base featuring a surface area (A) and
a culture medium disposed in the surface area of the base of the shallow-depth culture medium container up to a height (h) less than a height of the side walls of the container, wherein there is a ratio between the height (h), in meters, and the surface area (A), in square meters that meets the condition that $$\frac{h}{\sqrt[4]{A}} < 0.12 \; m^{1/2},$$

a rotation system equipped with rotating means comprising at least one set of blades, the so as to vertically displace the culture medium generating a turbulent regime in the culture medium, and a gas injection system which comprises diffusers that inject in the culture medium, air, $CO_2$ or mixtures of $CO_2$ with other combustion gases for the simultaneous transfer of both matter and heat, wherein the set of blades comprises a set of sweep blades further comprising brushes that contact the base of the container for re-suspending deposited algae and cleaning contaminations accumulated in the base of the container.

2. The microalgae culture system under external conditions according to claim 1, wherein it comprises a set of blades that generate light-darkness cycles in the culture medium.

3. The microalgae culture system under external conditions according to claim 1, wherein it comprises a set of deflector blades or blades equipped with deflection means.

4. The microalgae culture system under external conditions according to claim 1, wherein the gas injection system is located inside the area delimited by the culture medium container, extends from the centre to the periphery thereof along the entire radius and has the shape of a pit.

5. The microalgae culture system under external conditions according to claim 1, wherein the gas injection system is located inside the area delimited by the culture medium container and has the shape of a pit.

6. The microalgae culture system under external conditions according to claim 1, wherein the gas injection system is located outside the area delimited by the culture medium container, in the shape of a pit below the base of the container.

7. The microalgae culture system under external conditions according to claim 1, wherein the gas injection system is located outside the area delimited by the culture medium container and is placed at the level of the base of the container.

8. The microalgae culture system under external conditions according to claim 6, wherein it comprises a pump that allows for the exit of the culture from the container towards the gas injection system, and the return thereto.

9. The microalgae culture system under external conditions according to claim 4, wherein the gas injection system further comprises thermostatting means.

10. The microalgae culture system under external conditions according to claim 1, wherein the set of blades that generate the light-darkness cycles in the culture medium have a fin-shaped profile.

11. The microalgae culture system under external conditions according to claim 10, characterised in that the fin-shaped profile of the set of blades that generate the light-darkness cycles in the culture medium is such that the attack edge of the profile of the blades is closer to the bottom of the container than the outlet edge of said blades.

12. The microalgae culture system under external conditions according to claim 11, wherein the attack edge is not on the same vertical line as the outlet edge.

13. The microalgae culture system under external conditions according to claim 1, wherein the culture medium container has a circular base.

14. The microalgae culture system under external conditions according to claim 1, wherein it further comprises brushes in contact with the walls of the container for carrying the contaminations accumulated in the walls of the container.

15. The microalgae culture system under external conditions according to claim 1, wherein it further comprises a surface filtration system.

* * * * *